US00PP32226P3

(12) United States Plant Patent
Schoemaker

(10) Patent No.: US PP32,226 P3
(45) Date of Patent: Sep. 22, 2020

(54) ***HYDRANGEA* PLANT NAMED 'LC NO8'**

(50) Latin Name: *Hydrangea paniculata*
Varietal Denomination: LC NO8

(71) Applicant: Alex Frederick Schoemaker, Boskoop (NL)

(72) Inventor: Alex Frederick Schoemaker, Boskoop (NL)

( * ) Notice: Subject to any disclaimer, the term of this patent is extended or adjusted under 35 U.S.C. 154(b) by 0 days.

(21) Appl. No.: 16/602,281

(22) Filed: Sep. 6, 2019

(65) Prior Publication Data

US 2020/0084942 P1 Mar. 12, 2020

Related U.S. Application Data

(60) Provisional application No. 62/765,663, filed on Sep. 7, 2018.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

*Primary Examiner* — Susan McCormick Ewoldt
(74) *Attorney, Agent, or Firm* — C. A. Whealy

(57) ABSTRACT

A new and distinct cultivar of *Hydrangea* plant named 'LC NO8', characterized by its relatively compact and upright to broadly upright plant habit; moderately freely branching habit with strong lateral branches; freely flowering habit with plants remaining in flower for a long period time; dense and hardy inflorescences with white and red purple-colored sterile flowers that age attractively to greyed purple in color with development; and good garden performance.

2 Drawing Sheets

Figure 1:
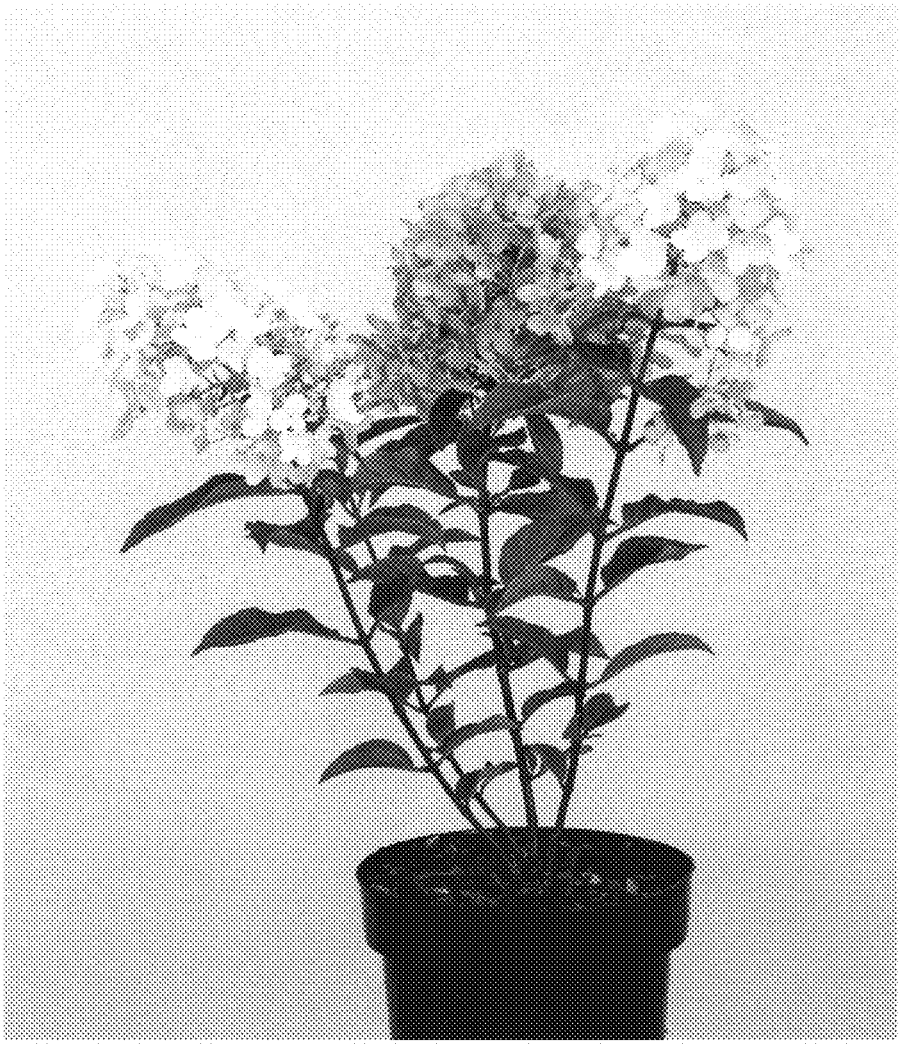

Botanical designation: *Hydrangea paniculata.*
Cultivar denomination: 'LC NO8'.

CROSS-REFERENCED TO CLOSELY RELATED APPLICATIONS

Title: Varieties of *Hydrangea* Plants
Applicant: Alex Frederick Schoemaker
Provisional application serial number: 62/765,663
Filed: Sep. 7, 2018
Title: *Hydrangea* Plant Named 'LC NO3'
Applicant: Alex Frederick Schoemaker
Filed: Concurrently with the instant application Ser. No. 16/602,288

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO8'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from a cross-pollination made by the Inventor in July, 2013 in Boskoop, The Netherlands, of *Hydrangea paniculata* 'Silver Dollar', not patented, as the female, or seed, parent with *Hydrangea paniculata* 'DVP Pinky', disclosed in U.S. Plant Pat. No. 16,166, as the male, or pollen, parent. The new *Hydrangea* plant was discovered and selected by the Inventor as a single flowering plant from within the progeny of the stated cross-pollination in a controlled greenhouse environment in Boskoop, The Netherlands during the summer of 2016.

Asexual reproduction of the new *Hydrangea* plant by vegetative tip cuttings in a controlled environment in Boskoop, The Netherlands since the summer of 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO8'. These characteristics in combination distinguish 'LC NO8' as a new and distinct *Hydrangea* plant:

1. Relatively compact and upright to broadly upright plant habit.
2. Moderately freely branching habit with strong lateral branches.
3. Freely flowering habit with plants remaining in flower for a long period time.
4. Dense and hardy inflorescences with white and red purple-colored sterile flowers that age attractively to greyed purple in color with development.
5. Good garden performance.

Plants of the new *Hydrangea* can be compared to plants of the female parent, 'Silver Dollar'. Plants of the new *Hydrangea* differ primarily from plants of 'Silver Dollar' in the following characteristics:

1. Plants of the new *Hydrangea* are more compact than and not as upright as plants of 'Silver Dollar'.
2. Inflorescences of plants of the new *Hydrangea* are more open than and not as dense as inflorescences of plants of 'Silver Dollar'.

Plants of the new *Hydrangea* can be compared to plants of the male parent, 'DVP Pinky'. Plants of the new *Hydrangea* differ primarily from plants of 'DVP Pinky' in inflorescence shape as inflorescences of plants of the new *Hydrangea* are distally more rounded than and distally not as pointed as inflorescences of plants of 'DVP Pinky'.

Plants of the new *Hydrangea* can be compared to plants of the *Hydrangea paniculata* 'LC NO3', disclosed in a U.S. Plant Patent application filed concurrently. In side-by-side comparisons, plants of the new *Hydrangea* differ primarily from plants of 'LC NO3' in plant habit as plants of the new *Hydrangea* are more compact, shorter and narrower than plants of 'LC NO3'. In addition, plants of the new *Hydrangea* grow more slowly than and are not as vigorous as plants of 'LC NO3'.

Plants of the new *Hydrangea* can also be compared to plants of the *Hydrangea paniculata* 'Phantom', not patented. In side-by-side comparisons, plants of the new *Hydrangea* differ primarily from plants of 'Phantom' in the following characteristics:

1. Plants of the new *Hydrangea* are more compact and broader than and not as tall and upright as plants of 'Phantom'.
2. Leaves of plants of the new *Hydrangea* are darker green in color than leaves of plants of 'Phantom'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'LC NO8'.

Figure 2:
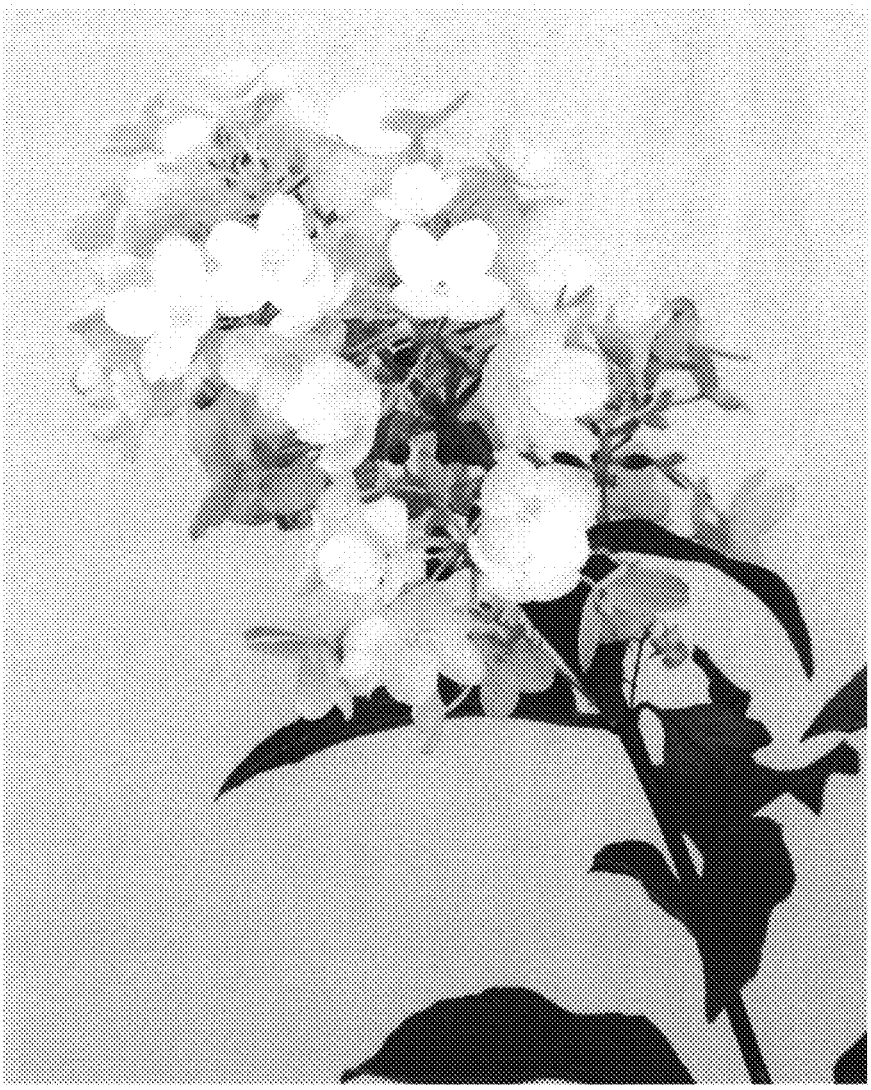

The photograph on the second sheet (FIG. 2 of 2) is a close-up view of a typical inflorescence of 'LC NO8'.

DETAILED BOTANICAL DESCRIPTION

Plants used in the aforementioned photographs and in the following description were grown during the late summer in 20-cm containers in an outdoor nursery in Boskoop, The Netherlands and under cultural practices typical of commercial *Hydrangea* production. During the production of the plants, day temperatures ranged from about 16° C. to 25° C. and night temperatures ranged from about averaged 5° C. to 16° C. Plants of the new *Hydrangea* were pinched one time and were two years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO8'.

Parentage:

*Female, or seed, parent.*—*Hydrangea paniculata* 'Silver Dollar', not patented.

*Male, or pollen, parent.*—*Hydrangea paniculata* 'DVP Pinky', disclosed in U.S. Plant Pat. No. 16,166.

Propagation:

*Type cutting.*—By vegetative tip cuttings.

*Time to initiate roots, summer.*—About 20 days at temperatures about 16° C. to 30° C.

*Time to produce a rooted young plant, summer.*—About 50 days at temperatures about 16° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact, upright to broadly upright plant habit; overall plant shape, obovate to broad inverted triangle; strong and sturdy stems; moderately vigorous growth habit and low growth rate.

*Plant height.*—About 43.9 cm.

*Plant diameter or area of spread.*—About 38.9 cm.

Lateral branch description:

*Branching habit.*—About six lateral branches develop per plant; pinching will enhance lateral branch development.

*Length.*—About 27.6 cm.

*Diameter.*—About 4 mm.

*Internode length.*—About 4.3 cm.

*Texture.*—When developing, moderately to densely pubescent; fully developed, woody.

*Aspect.*—Upright to about 20° from vertical.

*Strength.*—Strong, sturdy.

*Color.*—When developing: Close to 187B to 187C. Developed: Close to 200C to 200D; when woody, close to N199A and 200C.

*Lenticels.*—Density: Sparse; none observed on developing stems. Size, developed stems: About 1 mm by 0.5 mm. Color, developed stems: Close to 199D.

Leaf description:

*Arrangement.*—Opposite, simple.

*Length.*—About 9.2 cm.

*Width.*—About 4.6 cm.

*Shape.*—Ovate.

*Apex.*—Apiculate.

*Base.*—Short attenuate to obtuse.

*Margin.*—Serrate.

*Texture, upper surface.*—Slightly to moderately pubescent; not rugose.

*Texture, lower surface.*—Slightly to moderately pubescent; slightly scabrous; slightly rugose.

*Venation pattern.*—Pinnate.

*Color.*—Developing leaves, upper surface: Close to 143A. Developing leaves, lower surface: Close to 138B. Fully developed leaves, upper surface: Close to 137A; venation, close to 152B. Fully developed leaves, lower surface: Close to between 138A and 147B; venation, close to 194C, towards the base, strongly tinged with close to 180D.

*Petioles.*—Length: About 1.2 cm. Diameter: About 2 mm. Texture, upper surface: Smooth, glabrous; margins, moderately pubescent. Texture, lower surface: Smooth, glabrous; margins, sparsely pubescent. Color, upper surface: Close to 177A; towards the margins, close to 176A. Color, lower surface: Close to 145B; towards the margins, close to 176A.

Flower description:

*Flower type and habit.*—Showy sterile flowers and small inconspicuous fertile flowers arranged on terminal panicles; panicles ovate to broadly ovate in shape; sterile flowers face upright to outwardly and slightly drooping depending on their position in the inflorescence; fertile flowers face mostly upright.

*Fragrance.*—None detected.

*Natural flowering season.*—Flowering begins in the midsummer and is continuous until late summer in Northern Europe.

*Flower longevity.*—Sterile flowers last about six weeks on the plant, sterile flowers persistent; fertile flowers last about five days on the plant, fertile flowers not persistent.

*Quantity of flowers.*—Freely flowering habit; about 150 sterile flowers and about ten fertile flowers per panicle.

*Panicle height.*—About 17.6 cm.

*Panicle diameter.*—About 14.3 cm.

*Sterile flower buds.*—Length: About 5 mm. Diameter: About 7 mm. Shape: Cup-shaped to bowl-shaped. Color: Close to between 145D and 150D.

*Fertile flower buds.*—Length: About 4 mm. Diameter: About 3 mm. Shape: Obovate. Color: Close to 155C; towards the apex, close to 63C; immature calyx, close to 157C.

*Sterile flower diameter.*—About 3.4 cm.

*Sterile flower depth (height).*—About 1.1 cm.

*Fertile flower diameter.*—About 8 mm.

*Fertile flower depth (height).*—About 8 mm.

*Petals, sterile flowers.*—Quantity and arrangement: Four in a single whorl. Length: About 2.5 mm. Width: About 1.25 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155B; color does not change with development. When opening and fully opened, lower surface: Close to NN155B; distally, tinged with close to 59D; color does not change with development.

*Petals, fertile flowers.*—Quantity and arrangement: Five in a single whorl. Length: About 3 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155B; color does not change with development. When opening and fully opened, lower surface: Close to NN155B; color does not change with development.

*Sepals, sterile flowers.*—Quantity and arrangement: Typically four, occasionally five, in a single whorl. Length: About 1.7 cm. Width: About 1.5 cm. Shape: Broadly ovate to broadly obovate. Apex: Obtuse to emarginate. Base: Broadly cuneate. Margin: Entire. Texture and luster, upper and lower surfaces: Smooth, glabrous; matte. Color: When opening, upper surface: Close to 155A. When opening, lower surface: Close to 155C. Fully opened, upper surface: Close to between 155A and 157D; towards the apex, tinged with close to 59D; color becoming closer to 158D and 59D with subsequent development. Fully opened, lower surface: Close to 155A and 155C; towards the apex, tinged with close to 63C to 63D; color becoming closer to 160D, 59D and 185D with subsequent development.

*Sepals, fertile flowers.*—Quantity and arrangement: Five in a single whorl. Length: About 1.5 mm. Width: About 1.25 mm. Shape: Close to deltoid. Apex: Broadly acuminate. Base: Broadly cuneate. Margin: Entire. Texture and luster, upper and lower surfaces: Smooth, glabrous; matte. Color: When opening and fully opened, upper surface: Close to 157B; towards the apex, slightly tinged with close to 63D; color does not change with development. When opening and fully opened, lower surface: Close to 157B; towards the apex, slightly tinged with close to 63D; color does not change with development.

*Pedicels, sterile flowers.*—Length: About 2.4 cm. Diameter: About 1 mm. Strength: Moderately strong. Aspect: About 75° from branch axis. Texture and luster: Densely pubescent; matte. Color: Close to 145C to 145D.

*Pedicels, fertile flowers.*—Length: About 2 mm. Diameter: About 0.5 mm. Strength: Moderately strong. Aspect: About 20° from vertical. Texture and luster: Moderately pubescent; matte. Color: Close to 150D.

*Reproductive organs, sterile flowers.*—Stamens: Quantity per flower: About eight. Filament length: About 2.5 mm. Filament color: Close to 155C. Anther length: About 0.5 mm. Anther shape: Broadly oblong. Anther color: Close to 155A. Pollen amount: Moderate. Pollen color: Close to 156A. Pistils: To date, pistil development on sterile flowers of the new *Hydrangea* has not been observed.

*Reproductive organs, fertile flowers.*—Stamens: Quantity per flower: About ten. Filament length: About 4.5 mm. Filament color: Close to NN155D. Anther length: About 0.5 mm. Anther shape: Broadly oblong. Anther color: Close to 155A. Pollen amount: Moderate. Pollen color: Close to 156A. Pistils: Pistil quantity per flower: Typically two. Pistil length: About 1 mm. Stigma shape: Club-shaped. Stigma color: Close to 155A. Style length: About 0.5 mm. Style color: Close to 150D. Ovary color: Close to 157A.

*Seeds.*—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO8' as illustrated and described.

* * * * *